United States Patent [19]

Beavers

[11] Patent Number: 5,135,901
[45] Date of Patent: Aug. 4, 1992

[54] A CATALYST COMPOSITION COMPRISING RHODIUM, RUTHENIUM, AND A PROMOTER

[75] Inventor: William A. Beavers, Longview, Tex.

[73] Assignee: Eastman Chemical Company, Rochester, N.Y.

[21] Appl. No.: 711,771

[22] Filed: Jun. 7, 1991

Related U.S. Application Data

[62] Division of Ser. No. 568,150, Aug. 16, 1990, Pat. No. 5,043,480, which is a division of Ser. No. 372,797, Jun. 29, 1989, Pat. No. 4,973,741.

[51] Int. Cl.⁵ .................... B01J 23/64; B01J 27/185; B01J 27/24; B01J 23/46
[52] U.S. Cl. .................................... 502/161; 502/162; 502/325; 502/200; 502/213; 502/230; 502/201; 502/217; 502/170; 502/167; 502/233; 502/166
[58] Field of Search .............. 502/325, 200, 213, 230, 502/201, 217, 170, 161, 167, 162, 233, 166

[56] References Cited

U.S. PATENT DOCUMENTS

| | | | |
|---|---|---|---|
| 3,687,981 | 8/1972 | Lawrence et al. | 549/372 |
| 4,193,942 | 3/1980 | Gerritsen et al. | 502/166 X |
| 4,453,019 | 6/1984 | Chang | 502/166 X |
| 4,668,651 | 3/1987 | Billig et al. | 502/161 X |
| 4,719,145 | 1/1988 | Neely | 502/325 X |

Primary Examiner—W. J. Shine
Assistant Examiner—Douglas J. McGinty
Attorney, Agent, or Firm—Mark A. Montgomery; William P. Heath, Jr.; S. E. Reiter

[57] ABSTRACT

A catalyst used in a process for producing a β-hydroxyester product or a β-hydroxyaldehyde product from ethylene oxide, carbon monoxide, and, optionally, hydrogen, is disclosed. This process uses, as a catalyst, a catalyst comprising rhodium, ruthenium, and a Group Va promoter.

4 Claims, No Drawings

A CATALYST COMPOSITION COMPRISING RHODIUM, RUTHENIUM, AND A PROMOTER

This is a divisional of copending application Ser. No. 07/568,150 filed Aug. 16, 1990, now U.S. Pat. No. 5,043,480 which is a divisional of Ser. No. 372,797 filed Jun. 29, 1989 now U.S. Pat. No. 4,973,741 issued Nov. 27, 1990.

BACKGROUND OF THE INVENTION

1. Field of the Invention

The present invention relates to the production of β-hydroxyesters or β-hydroxyaldehydes from ethylene oxide and synthesis gas.

2. Discussion of the Background

The hydroformylation of ethylene oxide over cobalt catalysts has been known for some time to yield β-hydroxyaldehydes (see, e.g., "Organic Syntheses Via Metal Carbonyls," I. Wender and P. Pino (1968), John Wiley and Sons, Inc., pp 384–388; "Carbon Monoxide in Organic Synthesis;" J. Falbe, (1970), Springer-Verlag, pp 58–59). A major problem with this reaction, however, is that it only provides low yields of aldehydes. Attempting to increase yield of aldehydes using more forcing reaction conditions or longer reaction times produces aldol condensation products instead of the desired aldehyde products.

Rhodium is not known to catalyze the hydroformylation of ethylene oxide. It is known that rhodium promotes the carbonylation of ethylene oxide to produce β-lactones (see "Homogeneous Catalysis with Compounds of Rhodium and Iridium," by R. S. Dickson; D. Reidel Publishing House, 1985).

It is also known to promote the carbonylative ring opening of ethylene oxide in the presence of alcohols to yield β-hydroxypropionate esters as disclosed, for example, by Kawabata et al. in Nippon Kagaku Kaishi, 635 (1979). These authors disclose the use of dicobalt octacarbonyl/pyridine catalysts. The resulting products, at present, have limited utility, being used for the preparation of acrylate esters which in turn can be used for the preparation of acrylate resins and polyesters.

There is thus a distinct need for a process for readily producing useful products from ethylene oxide

OBJECTS OF THE INVENTION

Accordingly, one object of this invention is to provide a novel process for producing a β-hydroxyester product from ethylene oxide, carbon monoxide, hydrogen, and a primary alcohol.

It is another object of this invention to provide a novel process for producing a β-hydroxyaldehyde product from ethylene oxide, carbon monoxide, and hydrogen.

It is another object of this invention to provide a novel catalyst composition useful for catalyzing the transformation of ethylene oxide, carbon monoxide, and hydrogen into useful products.

These and other objects of the invention will become apparent from the description of the invention given herein below.

BRIEF DESCRIPTION OF THE INVENTION

In accordance with the present invention, there is provided a method for converting ethylene oxide into difunctional compounds having a three-carbon chain. These products include 1,3-disubstituted compounds and acrylates suitable for inclusion in any number of solvents, resins, and plastics.

The invention method is based on the carbonylation of ethylene oxide to β-hydroxypropionic acid derivatives, and optionally dehydrating the intermediate into acrylic acid derivatives. By selecting different alcohol functionalities to make the β-hydroxypropionic acid derivatives, the properties of these final products can be modified.

This invention encompasses a general method for producing difunctional compounds which have applications in such diverse areas as solvents, resins, coatings, and plastics. The catalyst system described herein is both versatile and more active than prior art catalysts known for these reactions. One basic catalyst formulation can be used for carbonylation, hydroformylation, or homologation giving good yields of each type of reaction product.

It has been discovered that a catalyst comprising the metals rhodium and ruthenium along with a Group Va promoter is capable of converting ethylene oxide into useful compounds having a three-carbon chain. Carrying out the reaction under different reaction conditions will produce different products in good selectivities Depending on the conditions selected, the main products obtained are β-hydroxyesters or β-hydroxyaldehydes. The conditions under which each of these products are predominantly formed is described in greater detail below.

DETAILED DESCRIPTION OF THE INVENTION

The catalyst composition provided by the present invention comprises (1) 100 parts of a rhodium component, (ii) 0.1 to $10^5$ parts of a ruthenium component, and (iii) 10 to $10^4$ parts of a promoter component. The rhodium component is a rhodium salt or a rhodium complex. The ruthenium component is a soluble homogenous ruthenium compound or a finely divided ruthenium metal. The promoter component is a nitrogen-containing compound, a phosphorus-containing compound, an arsenic-containing compound, or an antimony-containing compound.

The process for preparing a β-hydroxyproponate ester provided by the invention comprises contacting synthesis gas, ethylene oxide, a primary $C_{1-6}$ alkyl alcohol or benzyl alcohol, and a catalyst at a temperature from 40° C. to 120° C.; wherein the catalyst comprises rhodium, ruthenium, and a group Va promoter, and wherein the synthesis gas has a hydrogen to carbon monoxide molar ratio of from 0 to 0.5.

The process for preparing a β-hydroxypropionaldehyde (or its dimer, 2(β-hydroxyethyl)-4-hydroxy-1,3-dioxane) provided by the present invention comprises contacting synthesis gas, ethylene oxide, and a catalyst at a temperature of from 50° C. to 130° C.; wherein the catalyst comprises rhodium, ruthenium, and a Group Va promoter, and wherein the synthesis gas has a hydrogen to carbon monoxide molar ratio of from 0.3 to 3.0.

Any soluble form of rhodium is acceptable for the preparation of invention catalyst, including any insoluble form which will dissolve under the conditions of the reaction. These forms include rhodium salts such as rhodium nitrate, rhodium sulfate, rhodium chloride, rhodium bromide, rhodium iodide, rhodium fluoride, rhodium oxide, rhodium phosPhate, and the like; or organic rhodium salts such as rhodium formate, rhodium acetate, rhodium propionate, rhodium butyrate, and the like; or aromatic rhodium salts such as rhodium benzoate, rhodium phthalate, rhodium naphthenate, and the like. More preferable forms because of their greater solubilities are rhodium complexes including any of the rhodium carbonyls, rhodium(III)tris(2,4-pentanedionate), rhodium(I)dicarbonyl(2,4-pentanedionate), dirhodium tetracarbonyl dichloride, iodo rhodium(I)tris(triphenylphosphine), bromo rhodium(I)tris(triphenylphosphine), chloro rhodium(I)tris(triphenylphosphine), fluoro rhodium(I)tris(triphenylphosphine), rhodium(I)carbonyl chlorobis(triphenylphosphine), rhodium(I)hydrido carbonyl tris(triphenylphosphine), or other soluble rhodium complexes within the spirit of this group.

The concentrations of rhodium under which the invention reactions will take place are $10^{-6}$ molar to 10 molar more preferably $10^{-4}$ to 3 molar; and most preferably $10^{-2}$ molar to 1 molar.

The ruthenium component, which is optional for the production of β-hydroxyester products, but which is more important in the production of β-hydroxypropionaldehyde, should be present in concentrations dependent upon that of the primary rhodium component. It should be at least 0.001 to 1000 times the concentration of rhodium. More preferably, the concentration should be 0.02 to 50 times the rhodium concentration. The most preferred ruthenium concentrations are 0.5 to 10 times the rhodium concentration. The higher ruthenium concentrations should be present if reduced organic products are desired.

The form of the ruthenium is not as critical as that of the rhodium. Thus, it may be present in the form of a soluble homogeneous component or as a finely divided metal both of which are capable of catalyzing the reduction of organic functional groups although the different forms have different susceptibilities to inhibition by the Group Va promoters.

The soluble ruthenium components may be added in any of a number of forms including inorganic salts such as ruthenium nitrate, ruthenium sulfate, ruthenium fluoride, ruthenium chloride, ruthenium bromide, ruthenium iodide, ruthenium oxide, and ruthenium phosphate or organic ruthenium salts such as ruthenium formate, ruthenium acetate, ruthenium propionate, ruthenium butyrate, etc., or aromatic ruthenium salts such as ruthenium benzoate, ruthenium phthalate, ruthenium naphthenate, etc.

Ruthenium complexes are often more soluble than the salts and are, therefore, more desirable if high concentrations of homogeneous ruthenium solutions are desired. These complexes include ruthenium(III)-tris(2,4-pentanedionate), ruthenium(II)dichloro tris(triphenylphosphines), ruthenium(II)dichloro tetrakis-(triphenylphosphine), ruthenium(II)hydrido chloro tris(triphenylphosphine), or other soluble ruthenium complexes within the spirit of this group.

The insoluble or heterogeneous ruthenium forms may be introduced as any of the forms given above which under a sufficiently hydrogen rich atmosphere or reducing environment prior to the introduction of the soluble rhodium will give finely divided ruthenium. This method is the preferred one for giving the most highly divided ruthenium.

It may, however, be produced by reducing a soluble ruthenium form in the presence of a suitable support to give finely divided ruthenium deposited on supports including activated charcoal, alumina, silica gel, or zeolites. Other forms may be included if they can be divided finely enough by mechanical means such as ruthenium powder, ingot, shot, sponge, or wire. Of course, one preferred form, by analogy to its nickel analog, would be Raney ruthenium.

The Group Va promoter can be from any member of the series of elements including nitrogen, phosphorous, arsenic, or antimony. Preferably, the promoter used is present in their most reduced forms as tertiary organic derivatives.

Examples of suitable Group Va bond promoter catalysts include tertiary alkyl amines such as triethyl amine, tripropyl amine, tributyl amine, etc.; cyclic tertiary amines such as N-methyl piperidine, N-methylpyrrolidine, and 1,4-diazabicyclo[2,2,2]octane; tertiary aromatic amines such as triphenyl amine, trinaphthyl amine, etc.; mixed alkyl, aromatic, and alkyl-aromatic amines from the previous examples; and, pyridines.

Suitable phosphines include tertiary alkyl phosphines such as trimethyl phosphine, triethyl phosphine, tripropylphosphine, tributyl phosphine, trioctylphosphine, tricyclohexylphosphine, tribenzyphosphine, etc.; tertiary aromatic phosphines such as triphenylphosphine, tris(p-tolyl)-phosphine, tris (p-methoxyphenyl)-phosphine, tris(α-naphthyl)phosphine, etc.; and, mixed alkyl, aryl, or alkyl-aryl tertiary phosphines.

Suitable arsines include tertiary arsines such as triphenylarsine and suitable stibines include triphenylstibene.

The optimum concentration of these promotors depends on the concentration of the primary catalyst metal, rhodium. It should preferably be at least 0.1 to 100 times the molar concentration of the rhodium component; more preferably from 0.5 to 20 times the concentration; and most preferably from 1 to 10 times the molar concentration of rhodium. The reaction will take place outside of these constraints but at unacceptable rates due to either too little promoting effect for the very low concentrations or too great an inhibiting effect for the very high concentrations, especially during later hydrogenation reactions on heterogeneous ruthenium. For this same reason and the fact that the reactions run under more forcing conditions, the hydrogenated product, β-hydroxy propionaldehyde is prepared using the smaller amounts of the Group Va promoters within the preferred limits.

Production of β-Hydroxyester Products

For the preparation of β-hydroxypropionate ester products, synthesis gas, ethylene oxide, a primary $C_{1-6}$ alkyl alcohol or benzyl alcohol, and the catalyst provided by the present invention are contacted at a temperature from 40° C. to 120° C. The synthesis gas used will preferably have a hydrogen to carbon monoxide molar ratio from 0 to 0.5.

To optimize the yield of β-hydroxyester, the catalyst need be made of only soluble rhodium promoted with a Group Va promoter such as a tertiary amine. The presence of excess ruthenium is in no way detrimental to this reaction and in fact contributes marginally to the success of the reaction, although the reaction will take place entirely in its absence with no decrease in selectivity. The inertness of ruthenium toward detrimental side reactions is very important and leads to the success of the later reactions.

The primary $C_{1-6}$ alkyl alcohol used in accordance with this embodiment of the present invention is employed in an amount which is at least equimolar with the amount of oxirane used, but preferably higher amounts are used. For example, molar amounts of 1 to 10 times of oxirane may be used. The alcohol may also serve as the reaction solvent. The primary $C_{1-6}$ alkyl alcohol used can include methyl alcohol, ethyl 1 alcohol, n-propyl alcohol, n-butyl alcohol, n-pentyl alcohol, n-hexyl alcohol, 2-methyl-1-propanol, 2-methyl-1-butanol, 3-methyl-1-butanol, 2-methyl-1-pentanol, 3-methyl-1-pentanol, or 4-methyl-1-pentanol. The alcohol used may also be benzyl alcohol.

The reactions may be conducted with no additional solvent for the β-hydroxy propionate ester preparations. However, the preferred solvent is the alcohol portion of the ester. In this latter case, as noted above, at least one molar equivalent of the alcohol is required but up to a several fold excess of the alcohol may be used as solvent with no detrimental effect.

Of course, in all of these preparations, additional inert solvents may be utilized. Frequently, highly desirable effects are obtained in that the components of the reaction upon completion are extracted into different phases to keep the side reactions to a minimum. Included as suitable solvents are aliphatic hydrocarbons such as pentane, hexane, heptane, octane, and the like; aromatic hydrocarbons such as benzene, toluene, xylene, ethyl benzene, and the like; esters such as dimethyl ether, diethyl ether, dipropyl ether, dibutyl ether, tetrahydroduran, tetrahydropyan, and the like; halogenated solvents such as chloroform, carbon tetrachloride, tetrachloroethane, and the like; polar aquatic solvents such as sulfonane, and the like; as well as mixtures of any two or more thereof.

The conditions under which these reactions are conducted are very important and will in large part determine the product isolated. In order to prepare β-hydroxy propionate esters, ethylene oxide and the required alcohol are reacted at temperatures preferably from 40° C. to 120° C. A more preferable temperature is 50° C. to 100° C. and the most preferable temperature is 60° C. and 80° C.

Since this reaction is a pure carbonylation reaction, the synthesis gas used should be especially rich in carbon monoxide. The preferred synthesis gas composition has a hydrogen to carbon monoxide ratio ranging from 0 to 0.5. A more preferred range is 0 to 0.3 and the most preferred range is 0. to 0.1. Although this reaction is a pure carbonylation, a small amount of hydrogen appears to have an activating effect on the catalyst.

The synthesis gas should be used at pressures ranging from 500 to 10,000 psig. A more preferred range is 1,000 to 5,000 psig, and the most preferred range is 2,000 to 4,000 psig. Within the most preferred conditions and catalyst concentrations, these reactions are usually complete within 2 to 4 hours.

Preparation of β-Hydroxypropionaldehyde

To prepare β-hydroxypropionaldehyde, or more properly its dimer, 2(β-hydroxyethyl) 4-hydroxy-1,3-dioxane, the conditions need be only slightly more forcing than employed for preparation of β-hydroxy propionaldehyde, but the synthesis gas should be much richer in hydrogen. With or without a suitable solvent, other than an alcohol, the reaction takes place in a temperature range of 50° C. to 130° C. A more preferred range is 60° C. to 120° C. and the most preferred range is 70° C. to 100° C.

As is the case with the preparation of the β-hydroxypropionate ester, the catalyst need not contain the ruthenium component but must contain the rhodium and the promoter components.

The preferred synthesis gas ratios employed in accordance with this embodiment of the present invention are a hydrogen to carbon moroxide ratio of 0.3 to 3. More preferred ratios are 0.5 to 2; with the most preferred ratio being 0.7 to 1.5.

The pressure under which this synthesis gas is utilized is the same as for the preparation of β-hydroxy propionate esters, which is 500 to 10,000 psig. A more preferred pressure is 1,000 to 5,000 psig, and the most preferred pressure range is 2,000 to 4,000 psig. Under these most preferred conditions and catalyst concentration, the reaction is usually complete within 0.5 to 2 hours.

It is desirable, in order to optimize formation of β-hydroxy propionaldehyde, that ethylene oxide conversions are maintained below about 30%. While reaction continues at conversions above 30% at such higher conversions, the selectivity to the desired product falls off as a result of further reaction with by-product water (formed by dehydration of the hydroxy-aldehyde intermediate). In addition, by-product water can also react with ethylene oxide to produce other by-product materials.

This invention provides a new method for making a range of carbonylation and/or hydrogenative carbonylation difunctional products from ethylene oxide using a novel ruthenium/rhodium catalyst. While the usual catalyst for this type reaction is based on cobalt, it has surprisingly been discovered that rhodium is about ten times more active than cobalt for the carbonylation and hydroformylation reactions, and that ruthenium is about five times more active for the hydrogenation. The combined ruthenium/rhodium catalyst is, therefore, up to fifteen times more active for converting ethylene oxide into desirable difunctional products.

The mode of action of cobalt during its catalysis of synthesis gas condensation with ethylene oxide would lead to the conclusion that rhodium or ruthenium based catalyst would be far less effective. Indeed the activity of rhodium or ruthenium catalysts is less than one-third that of cobalt catalysts in the absence of the Group Va promoter. Introduction of this promoter causes the course of the reaction to change entirely so that the combination of rhodium/ruthenium is much more active. The combination of rhodium and ruthenium in this catalyst extends its versatility so that a variety of products are accessible.

Other features of the invention will become apparent in the course of the following description of exemplary embodiments which are given for illustration of the invention and are not intended to be limiting thereof.

EXAMPLE 1 METHYL β-HYDROXYPROPIONATE

To a nitrogen flushed 300 mL Hastelloy C autoclave was charged 2.5 mmole of rhodium(I)hydrido carbonyl tris(triphenylphosphine), 10 mmole of ruthenium(III)-tris(2,4-pentanedionate), 37.5 mmole of triethylamine, 50 mL of anhydrous methanol, and 50 mL of ethylene oxide. The head was torqued on and the contents were stirred rapidly while the autoclave was charged to 2,000 psig with carbon monoxide. The solution was then heated to 70° C. During this time, the pressure increased to 2,200 psig and was maintained at that level by periodic recharging from an external reservoir. The reaction was conducted for a total of 4 hours during which time the total pressure drop mounted to 1,050 psig. Analysis of the product upon completion of the reaction revealed a ethylene oxide conversion of 90.3 percent with selectivity to methyl β-hydroxypropionate of 66.0 percent, β-methoxypropionate of 3.0 percent, β-hydroxypropionic acid of 2.4 percent, methyl (β-hydroxyethoxy)propionate of 12.3 percent, and 11.0 percent miscellaneous.

EXAMPLE 2 METHYL β-HYDROXYPROPIONATE

To a nitrogen flushed 300 mL Hastelloy B autoclave was charged 2.5 mmole of rhodium(II)bis(2-ethylhexanoate), 10 mmole of ruthenium(III)tri(2,4 pentanedionate), 5 mmole of α,α'-bipyridyl, 50 mL anhydrous methanol, and 50 mL ethylene oxide. The head was torqued on and the contents were stirred and charged to 2,000 psig with carbon monoxide. The temperature was raised to 70° C. at which point the pressure had climbed to 2,200 psig. It was maintained at this level by periodic recharging from an external reservoir. The reaction was conducted for 4 hours during which time the pressure dropped by 150 psig. Analysis of the product mixture revealed a conversion of 26.3 percent with the selectivity to methyl β-hydroxypropionate of 43.5 percent, to β-methoxyethanol of 6.4 percent, to methyl β-methoxypropionate of 4.4 percent, to β-hydroxypropionic acid of 4.6 percent, to methyl β-(2-hydroxyethoxy)propionate of 22.1 percent, and 19.0 percent miscellaneous.

EXAMPLE 3 METHYL β-HYDROXYPROPIONATE

To a nitrogen flushed 300 mL Hastelloy C autoclave was charged 2.5 mmole of hydrido carbonyl rhodium-(I)tris(triphenylphosphine), 10 mmoles of ruthenium-(III)tris(2,4-pentanedionate), 10 mmole triphenylphosphine, 50 mL absolute methanol, and 50 mL ethylene oxide. The head was torqued on and the contents were stirred and charged with 2,000 psig of carbon monoxide. The autoclave was heated to 70° C at which point the pressure rose to 2,200 psig at which level it was maintained by periodic recharging from an external reservoir. The reaction was conducted 4 hours during which time the pressure drop amounted to 400 psig. Analysis of the product mixture revealed a conversion of 31.2 percent with the selectivity to methyl β-hydroxypropionate of 17.4 percent β-methoxyethanol of 31.9 percent, methyl β-methoxypropionate of 18.4 percent, βhydroxypropionic acid of 6.4 percent methyl (β-hydroxyethoxy)propionate of 4.0 percent, methyl acrylate 9.7 percent, and 12.2 percent miscellaneous.

EXAMPLE 4 β-HYDROXYPROPIONALDEHYDE

To a nitrogen flushed 300 mL Hastelloy C autoclave was charged 2.5 mmole of hydrido carbonyl rhodium-(I)tris(triphenylphosphine), 10 mmole of ruthenium-(III)tris(2,4-pentanedionate), 17.5 mmole triphenylphosphine, and 100 mL ethylene oxide. The head was torqued on and the contents were stirred and the autoclave charged with 2,000 psig of synthesis gas ($H_2$/CO=1/1). The contents were heated to 80° C. at which point the pressure had climbed to 2,200 psig. The pressure was maintained at this level throughout the reaction by periodic recharging from an external reservoir. The reaction was conducted for 6 hours during which the pressure drop amounted to 950 psig. Analysis of the product upon completion of the reaction revealed an ethylene oxide conversion of 28.5 percent with the selectivity to β-hydroxypropionaldehyde of 74.5 percent, to ethanol of 20 3 percent, to propionaldehyde of 2.2 percent, and 3.0 percent miscellaneous.

EXAMPLE 5 β-HYDROXYPROPIONALDEHYDE

To a nitrogen flushed 300 mL Hastelloy C autoclave was charged 2.5 mmole hydrido carbonyl rhodium(I)-tris(triphenylphosphine), 10 mmole ruthenium(III)-tris(2,4-pentanedionate), 15 mmole triethylamine, and 100 mL ethylene oxide. The head was torqued on and the contents were stirred and the autoclave was charged with 2,000 psig of synthesis gas ($H_2$/CO=1/1). The contents were heated to 80° C. at which point the pressure had climbed to 2,200 psig. The pressure was maintained at this level throughout the reaction by periodic recharging from an external reservoir. The reaction was conducted for 4 hours during which time the pressure drop amounted to 650 psig. Analysis of the product upon completion of the reaction revealed an ethylene oxide conversion of 29.4 percent with the selectivity to β-hydroxypropionaldehyde dimer of 89.7 percent, to ethanol of 5.6 percent, to propionaldehyde of 2.5 percent, and 2.2 percent miscellaneous. EXAMPLE 6 β- HYDROXYPROPIONALDEHYDE To a nitrogen flushed 300 mL Hastelloy B autoclave was charged 2.5 mmole hydrido carbonyl rhodium(I)-tris(triphenylphosphine), 10 mmole ruthenium(III)-tris(2,4-pentanedionate), 12.5 mmole α,α'-bipyridyl, and 100 mL ethylene oxide. The head was torqued on and the contents were stirred and the autoclave was charged with 2,000 psig of synthesis gas ($H_2$/CO=1/1). The contents were heated to 80° C. at which point the pressure had climbed to 2,200 psig. At this point, the synthesis gas pressure was raised to 3,000 psig and maintained at this level periodic recharging from an external reservoir. The reaction was conducted for 6 hours during which time the pressure drop amounted to 725 psig. Analysis of the product mixture revealed an ethylene oxide conversion of 27.3 percent with the selectivity to β-hydroxypropionaldehyde dimer of 67.0 percent, to ethanol of 10.9 percent, to propionaldehyde of 11.6 percent, to ethylene glycol of 4.2 percent, to 1-propanol of 1.5 percent, and 4.8 percent miscellaneous.

Obviously, numerous modifications and variations of the present invention are possible in light of the above teachings. It is therefore to be understood that within the scope of the appended claims, the invention may be practiced otherwise than as specifically described herein.

We claim:
1. A catalyst composition comprising:
   (i) a rhodium component,
   (ii) a ruthenium component 0.001 to 1000 times the molar concentration of said rhodium component, and
   (iii) a promoter component 0.1 to 100 times the molar concentration of said rhodium component;
   wherein said rhodium component is a rhodium salt or a rhodium complex,
   wherein said rhodium component is soluble homogeneous ruthenium compound or a finely divided ruthenium metal, and
   wherein said promoter component is a nitrogen-containing compound, a phosphorus-containing compound, an arsenic-containing compound, or an antimony-containing compound.
2. The catalyst composition of claim 1 wherein said rhodium component is at least one member selected from the group consisting of rhodium nitrate, rhodium sulfate, rhodium chloride, rhodium bromide, rhodium iodide, rhodium fluoride, rhodium oxide, rhodium phosphate, rhodium formate, rhodium acetate, rhodium propionate, rhodium butyrate, rhodium benzoate, rhodium phthalate, rhodium naphthenate, rhodium carbonyls, rhodium(III)tris(2,4-pentanedionate), rhodium(I)dicarbonyl(2,4-pentanedionate), dirhodium tetracarbonyl dichloride, iodo rhodium(I)tris(triphenylphosphine), bromo rhodium(I)tris(triphenylphosphine), chloro rhodium(I)tris(triphenylphosphine), fluoro rhodium(I)tris(triphenylphosphine), rhodium(I)carbonyl chlorobis(triphenylphosphine), and rhodium(I)hydridocarbonyl tris(triphenylphosphine).

3. The catalyst composition of claim 1 wherein said ruthenium component is at least one member selected from the group consisting of ruthenium nitrate, ruthenium sulfate, ruthenium fluoride, ruthenium chloride, ruthenium bromide, ruthenium iodide, ruthenium oxide, ruthenium phosphate, ruthenium formate, ruthenium acetate, ruthenium propionate, ruthenium butyrate, ruthenium benzoate, ruthenium phthalate, ruthenium naphthenate, ruthenium(III)tris(2,4-pentanedionate), ruthenium(II)dichloro tris(triphenylphosphine), ruthenium(II)dichloro tetrakis(triphenylphosphine), and ruthenium(II)hydrido chloro tris(triphenylphosphine).

4. The catalyst composition of claim 1 wherein said promoter component is at least one member selected from the group consisting of triethyl amine, tripropyl amine, tributyl amine, N-methyl piperidine, N-methylpyrrolidine, 1,4-diazabicyclo[2,2,2]octane, triphenyl amine, trinaphthyl amine, pyridines, trimethyl phosphine, triethyl phosphine, tripropylphosphine, tributyl phosphine, trioctylphosphine, tricyclohexylphosphine, tribenzyphosphine, triphenylphosphine, tris(p-tolyl)phosphine, tris (p-methoxyphenyl)phosphine, tris (α-naphthyl)phosphine, triphenylarsine, and triphenylstibine.

* * * * *